(12) United States Patent
Ashida et al.

(10) Patent No.: US 9,249,318 B2
(45) Date of Patent: *Feb. 2, 2016

(54) DISPERSION

(75) Inventors: Takuro Ashida, Osaka (JP); Kunitada Nishida, Osaka (JP); Jun Iwata, Fukushima (JP)

(73) Assignee: Sakai Chemical Industry Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/235,585

(22) PCT Filed: Aug. 1, 2012

(86) PCT No.: PCT/JP2012/069582
§ 371 (c)(1),
(2), (4) Date: Mar. 26, 2014

(87) PCT Pub. No.: WO2013/018827
PCT Pub. Date: Feb. 7, 2013

(65) Prior Publication Data
US 2014/0199251 A1 Jul. 17, 2014

(30) Foreign Application Priority Data

Aug. 3, 2011 (JP) ................................ 2011-169746
Apr. 5, 2012 (JP) ................................ 2012-086087

(51) Int. Cl.

| | |
|---|---|
| *A61K 8/00* | (2006.01) |
| *C09D 11/02* | (2014.01) |
| *A61K 8/27* | (2006.01) |
| *A61Q 17/04* | (2006.01) |
| *C09D 5/02* | (2006.01) |
| *C09D 7/12* | (2006.01) |
| *C09D 17/00* | (2006.01) |
| *C09D 201/00* | (2006.01) |
| *A61K 8/29* | (2006.01) |
| *A61K 8/02* | (2006.01) |
| *A61K 8/04* | (2006.01) |
| *A61K 8/19* | (2006.01) |
| *C09D 11/037* | (2014.01) |

(52) U.S. Cl.
CPC .............. *C09D 11/02* (2013.01); *A61K 8/0241* (2013.01); *A61K 8/04* (2013.01); *A61K 8/19* (2013.01); *A61K 8/27* (2013.01); *A61K 8/29* (2013.01); *A61Q 17/04* (2013.01); *C09D 5/02* (2013.01); *C09D 5/024* (2013.01); *C09D 7/12* (2013.01); *C09D 7/1225* (2013.01); *C09D 7/1266* (2013.01); *C09D 11/037* (2013.01); *C09D 17/00* (2013.01); *C09D 201/00* (2013.01); *A61K 2800/612* (2013.01); *A61K 2800/651* (2013.01)

(58) Field of Classification Search
None
See application file for complete search history.

(56) References Cited

U.S. PATENT DOCUMENTS

| | | |
|---|---|---|
| 2003/0228271 A1 | 12/2003 | Batz-Sohn et al. |
| 2007/0078200 A1 | 4/2007 | Yoshida et al. |
| 2008/0044483 A1 | 2/2008 | Kessell |
| 2008/0173216 A1 | 7/2008 | Tsutsui et al. |
| 2008/0188574 A1 | 8/2008 | Lee et al. |
| 2008/0226727 A1 | 9/2008 | Kessell et al. |
| 2009/0252774 A1 | 10/2009 | Kamei et al. |
| 2013/0046028 A1* | 2/2013 | Deeth et al. ................. 514/777 |

FOREIGN PATENT DOCUMENTS

| | | | |
|---|---|---|---|
| DE | 19645317 A1 | 5/1998 | |
| GB | 847007 A | 9/1960 | |
| JP | H0-7247119 A | 9/1995 | |
| JP | 10-167946 * | 6/1998 | ............... A61K 7/42 |
| JP | H11-147714 A | 6/1999 | |
| JP | 2000-072623 A | 3/2000 | |
| JP | 2004-002887 A | 1/2004 | |

* cited by examiner

*Primary Examiner* — Hasan Ahmed
(74) *Attorney, Agent, or Firm* — Novak Druce Connolly Bove + Quigg LLP (57) ABSTRACT

An object of the present invention is to obtain a dispersion in which a water-repellent inorganic powder is dispersed in water. The dispersion can be handled easily because the dispersion medium is water. In the case of using the dispersion for cosmetics, the dispersion can be suitably used when an inorganic powder subjected to a water-repellent treatment is mixed in an aqueous cosmetic. A dispersion in which an inorganic powder subjected to a water-repellent organic surface treatment is uniformly dispersed in water, wherein the contents of a water-repellent inorganic powder, a dispersant, and water is 80% by weight or more based on the total amount of the dispersion.

19 Claims, 3 Drawing Sheets

DISPERSION

CROSS REFERENCE TO RELATED APPLICATIONS

This application is a National Phase filing under 35 U.S.C. §371 of PCT/JP2012/069582 filed on Aug. 1, 2012; and this application claims priority to Application No. 2011-169746 filed in Japan on Aug. 3, 2011 and Application No. 2012-086087 filed in Japan on Apr. 5, 2012; the entire contents of all are hereby incorporated by reference.

TECHNICAL FIELD

The present invention relates to a dispersion in which an inorganic powder subjected to a water-repellent organic surface treatment is dispersed in water.

BACKGROUND OF THE DISCLOSURE

Inorganic powders, for example, zinc oxide or titanium oxide microparticles having a particle diameter of several tens to a hundred of nanometers, have been often used as an additive for sunscreen cosmetics, inks for exterior applications, food packaging materials, and the like because of their properties. When these powders are untreated, since the surfaces are hydrophilic, these powders may flow off by sweat or rain. Therefore, particularly in cosmetic applications, these powders are often used by subjecting the surfaces thereof to a water-repellent treatment with a silicone or a metallic soap.

On the other hand, since primary particles of inorganic powders generally tend to aggregate, the powders have been widely used by dispersing the powders in a dispersion medium, as described in Patent Document 1 or Patent Document 2, in order to exert sufficiently the visible light transparency and ultraviolet blocking performance of zinc oxide or titanium oxide microparticles. However, in conventional dispersions, water-repellent powders have been dispersed in oils, and hydrophilic powders have been dispersed in water, alcohol, glycol, or the like.

If an inorganic powder subjected to a water-repellent treatment can be dispersed in water, an effect by a powder subjected to a water-repellent treatment as described above can be obtained when a water-based composition is used for various applications. However, the attempt has been scarcely tried. In addition, if a water-repellent powder can be dispersed in water, dispersions can be used without caring laws and regulations and hazardousness because of free of any flammable organic solvent.

In the field of coating, it is known that a pigment dispersing resin is used when a pigment is mixed in a water-based coating (for example, Patent Document 3). However, in the pigment dispersed paste of Patent Document 3, the pigment is not subjected to a water-repellent treatment. Also, in Patent Document 3, since the inorganic powder as a raw material is used in powder form, and the powder and other components are mixed and dispersed with the pigment dispersing resin, the powder is not designed to prevent the aggregation between particles sufficiently, and there is a problem that the physical properties tend to change depending on the raw materials. Further, since various resins or pigments are added to the powder, the powder is deficient in applicability, and has a difficulty for use as a raw material.

Further, one method has been performed that a thin film of an inorganic powder is formed by using a dispersion of an inorganic powder to make a coating film, and subjecting the obtained thin film to a heat treatment or a plasma treatment. In the formation of a thin film, the method has an advantage that a thin film can be formed without the risk of ignition because use of any solvent is not required by using an aqueous dispersion of an inorganic powder.

PRIOR TECHNICAL DOCUMENTS

Patent Documents

[Patent Document 1] Japanese Kokai Publication Hei 11-147714
[Patent Document 2] Japanese Kokai Publication 2004-2887
[Patent Document 3] Japanese Kokai Publication 2008-195925

SUMMARY OF INVENTION

Problem to be Solved by the Invention

An object of the present invention is to obtain a dispersion in which a water-repellent inorganic powder is dispersed in water. The dispersion can be handled easily because the dispersion medium is water. In the case of using the dispersion for cosmetics, the dispersion can be suitably used when an inorganic powder subjected to a water-repellent treatment is mixed in an aqueous cosmetic. Another object of the present invention is to provide a dispersion from which a thin film of an inorganic powder can be formed without the risk of ignition by a heat treatment or a plasma treatment after the formation of the coating film with the dispersion.

Means for Solving Object

The present invention relates to a dispersion in which an inorganic powder subjected to a water-repellent organic surface treatment is uniformly dispersed in water, wherein the contents of a water-repellent inorganic powder, a dispersant, and water is 80% by weight or more based on the total amount of the dispersion.

The water-repellent inorganic powder is preferably an inorganic oxide surface-treated with a water-repellent material, the inorganic oxide having ultraviolet absorption and scattering properties.

The water-repellent inorganic powder is preferably an inorganic oxide surface-treated with a reactive surface treating agent.

The reactive surface treating agent is preferably at least one selected from the group consisting of a silicone, a silane-based treating agent, and a titanate-based treating agent.

The water-repellent inorganic powder is preferably at least one selected from the group consisting of titanium oxide, zinc oxide, iron oxide, cerium oxide, and composites thereof.

The amount of the water-repellent inorganic powder is preferably from 10 to 60% by weight based on the total amount of the dispersion.

Preferably, a dispersant having an HLB value of 10 to 17 is used as the dispersant for the dispersion of the present invention.

The amount of the dispersant is preferably from 2 to 15% based on the total amount of the dispersion.

The dispersion of the present invention may further comprises a preservative.

The preservative is preferably a polyhydric alcohol.

The polyhydric alcohol is preferably at least one compound selected from the group consisting of propylene glycol, butylene glycol, dipropylene glycol, pentylene glycol, and hexylene glycol.

The dispersion of the present invention may not contain any components other than the water-repellent inorganic powder, the dispersant, water, and the preservative.

The present invention relates to a cosmetic obtained by mixing the above-mentioned dispersion with any other component.

The present invention relates to a water-based coating obtained by mixing the above-mentioned dispersion with any other component.

The present invention relates to a water-based ink composition obtained by mixing the above-mentioned dispersion with any other component.

Effect of the Invention

Since the dispersion of the present invention is a dispersion in which an inorganic powder subjected to a water-repellent organic surface treatment is uniformly dispersed in water, the dispersion can be handled easily, and an inorganic powder subjected to a water-repellent treatment can be easily mixed in an aqueous composition in the fields of cosmetics, coatings, and inks. Further, when used in the production of inorganic thin films, the dispersion is preferred also in terms of no risk of ignition. Further, in a powder without being subjected to a water-repellent organic surface treatment, a hydroxyl group is present on the surface of the powder, and the powder may aggregate strongly after drying the dispersion; however, when the aqueous dispersion of the present invention is dried, since the amount of the hydroxyl group at the surface of the powder is remarkably small, a smooth film can be produced.

DETAILED DESCRIPTION OF PREFERRED EMBODIMENTS

Examples of the inorganic powder used in the present invention include, but not limited to, commonly used zinc oxide, titanium oxide, cerium oxide, iron oxide, barium sulfate, calcium carbonate, silica, aluminium hydroxide, alumina, boron nitride, talc, mica, and kaolin. Particularly preferred examples of the inorganic powder include inorganic powders having ultraviolet absorption and scattering properties, including titanium oxide, zinc oxide, iron oxide, cerium oxide, and composites thereof. The composite refers to, for example, a powder in which other inorganic particles are dispersed in a surface-treated powder or an inorganic powder.

Since the inorganic powder having an ultraviolet blocking effect is generally used in the cosmetic application, the inorganic powder is preferred because the powder can be easily mixed in an aqueous cosmetic. Further, the inorganic powder is preferred because an inorganic thin film having an ultraviolet blocking effect can be easily formed by using the inorganic powder. Among them, zinc oxide and titanium oxide are particularly preferred.

The inorganic powder may be used as a combination of two or more inorganic powders.

The inorganic powder used in the present invention may be a composite powder obtained by covering the surface of the inorganic powder with any other inorganic material. In this case, the surface treating material may be any known inorganic surface treating material, for example, zinc oxide, titanium oxide, cerium oxide, iron oxide, barium sulfate, hydrated silica, silica, aluminium hydroxide, and alumina. The covering amount is preferably from 1% by weight to 25% by weight based on the total amount of the inorganic powder.

When the inorganic powder is ultraviolet blocking particles, the average particle diameter is preferably from 10 to 200 nm. The ultraviolet blocking particles having the above-mentioned particle diameter are particularly preferred in view of having high visible light transparency and a suitable ultraviolet blocking region. If the particle diameter is more than 200 nm, the visible light transparency may be deteriorated, and the ultraviolet blocking performance may be deteriorated. In addition, if the particle diameter is less than 10 nm, the inorganic powder is undesirable in view of the possibility of deteriorating the ultraviolet blocking performance. Further, when the inorganic powder is not ultraviolet blocking particles, or when the ultraviolet blocking property is not required, the particle diameter has only to be an optimal size for utilization of the particles. The particle diameter of the inorganic powder is measured by measuring the particle diameters of randomly selected 200 particles with an electron microscope, and calculating the average particle diameter of the primary particles.

The shape of the inorganic powder is not particularly limited, and a powder having any shape can be used, including spherical, rod-shaped, needle-shaped, spindle-shaped, and plate-shaped powders. In rod-shaped, needle-shaped, or spindle-shaped particles, the average particle diameter is defined as the length in the direction of the short axis. In plate-shaped particles, the average particle diameter is defined as the average of the length in the direction of the diagonal line of the plane.

The type of the water-repellent organic surface treatment of the inorganic powder is not particularly limited, and any known method can be used. The water-repellent organic surface treatment is a treatment in which affinity of the surface of the inorganic powder with water is decreased, and any surface treatment with a material being water-soluble or water-dispersible after the treatment is not included in the "water-repellent treatment" of the present invention.

More specific examples of the water-repellent organic surface treatment include, for example, a treatment with methyl hydrogen polysiloxane, dimethyl polysiloxane, an alkylsilane, an alkyl titanate, a metallic soap, or an amino acid.

The water-repellent organic surface treatment is preferably a treatment with a reactive surface treating agent such as a silicone, a silane-based treating agent, or a titanate-based treating agent. The use of the reactive surface treating agent is particularly preferred because the surface treating agent is not isolated from the inorganic powder. If the surface treating agent is isolated from the inorganic powder, the inorganic powder aggregates, which is undesirable.

Examples of the silicone include any known silicone having a hydrogen-silicon bond, including methyl hydrogen polysiloxane, (dimethicone/methicone)copolymer. Other examples of the silicone include triethoxysilylethyl polydimethylsiloxyethyl dimethicone (KF-9908 manufactured by Shin-Etsu Chemical Co., Ltd.), and triethoxysilylethyl polydimethylsiloxyethyl hexyl dimethicone (KF-9909 manufactured by Shin-Etsu Chemical Co., Ltd.), which have an alkoxy group-silicon bond as a reactive group. Further, dimethyl polysiloxane can be mentioned, although the treatment condition needs to be severe in order to increase the reactivity.

Examples of the silane-based treating agent include a silylation agent having an organic group introduced therein, and a silane coupling agent, for example, triethoxycaprylylsilane.

Examples of the titanate-based treating agent include titanium coupling agents, such as alkyl titanate, pyrophosphoric acid type titanate, phosphorous acid type titanate, and amino acid type titanate.

In the water-repellent organic treatment of the inorganic powder, from 2 to 12% by weight of the total amount of the inorganic powder after treatment is preferably subjected to the water-repellent organic treatment. If the amount of the inorganic powder subjected to the water-repellent organic surface treatment is less than 2% by weight, it is undesirable in view of insufficient water repellency. If the amount is more than 12% by weight, it is undesirable because the effect of water repellency is saturated, and the cost is increased in vain. In the water-repellent treatment, from 3 to 10% by weight of the total amount of the inorganic powder is more preferably subjected to the water-repellent treatment.

The dispersion preferably contains the inorganic powder in an amount of 10 to 60% by weight based on the total amount of the dispersion.

The dispersion of the present invention contains a dispersant. Thus, the inorganic particles subjected to a water-repellent treatment successfully can be dispersed uniformly in a water-based medium. Types of the dispersant which can be used in the present invention include, but not limited to, for example, a polycarboxylic acid or a salt thereof, an alkyl sulfonic acid or a salt thereof, an alkyl benzene sulfonic acid or a salt thereof, a naphthalenesulfonic acid or a salt thereof, a polyether alkyl sulfonic acid or a salt thereof, an alkylbetaine, a polyether or a derivative thereof, a polyether alkyl ether, a polyoxyalkylene alkenyl phenyl ether, a sorbitan fatty acid ester, a polyether sorbitan fatty acid ester, a polyether fatty acid ester, a glycerin fatty acid ester, a polyether hydrogenated castor oil, a polyetheralkylamine, a polyether-modified silicone, a polyglycerin-modified silicone, a polyhydric alcohol, and an alkyl-modified polyhydric alcohol. Although any one of an anionic, cationic, and nonionic dispersants can be used, a nonionic dispersant is preferred in order to prevent the chemical reaction with the inorganic powder. The dispersion may be used as a combination of two or more dispersions.

Among them, a polyether-modified silicone and/or a polyether sorbitan fatty acid ester is particularly preferred. A polyether-modified silicone can be particularly suitably used in the present invention because the silicone has high thermal stability and safety.

The dispersant preferably has an HLB value of 10 to 17. If the HLB value is out of the range, the powder may be dispersed insufficiently, and various physical properties such as ultraviolet blocking performance may be affected. In the present invention, the HLB value is calculated by the following expression as defined by W. C. Grifinn:

$$N_{HLB}=(E+P)/5$$

($N_{HLB}$: HLB value, E: % by weight of a polyoxyethylene moiety based on the whole molecules of the dispersant, P: % by weight of a polyhydric alcohol moiety based on the whole molecules of the dispersant)

The amount of the dispersant is preferably from 2 to 15% by weight based on the total amount of the dispersion. If the amount is less than the range, the powder is hard to blend in water. If the amount is more than the range, it is disadvantages in cost.

In the dispersion of the present invention, the amount of the inorganic powder, the dispersant, and water is 80% by weight or more based on the total amount of the dispersion. That is, preferably, 80% by weight or more of the total amount of the composition is any of these three components, and more preferably, 90% by weight or more of the total amount of the composition is any of these three components. In the dispersion of the present invention, an inorganic powder subjected to a hydrophobization treatment can be used as a raw material in the compositions for cosmetics, coatings, and inks. Therefore, if other components are blended, when the dispersion of the present invention is used as a raw material, some extra compound is present in the dispersion. For example, if the dispersion is mixed in a cosmetic, the dispersion can not be used when the dispersion includes any undesirable compound, which is undesirable in view of deficiency in applicability.

Further, it is also undesirable in view of the possibility of undesirable performance with any other component used in the formulation.

The dispersion of the present invention does not contain any component other than the three components as described above in an amount exceeding 20% by weight. The dispersion may contain not more than 20% by weight of any other component unless the performance of the dispersion is deteriorated. More preferably, the dispersion may contain not more than 10% by weight of any other component. However, it is preferred that any compound having a possibility of deteriorating the stability of the dispersion is not added.

Examples of the component which may be added include, but not limited to, a preservative. That is, the dispersion containing the components may decay depending on the condition and period of storage. In order to prevent the decay, a preservative may be added. Examples of the preservative include, but not limited to, for example, glycol-based preservatives such as propylene glycol, butylene glycol, dipropylene glycol, pentylene glycol, and hexylene glycol; parabenzoic acid esters such as methyl paraoxybenzoate; piroctone olamine, phenoxyethanol, and polyglyceryl-3 caprylate. The preservative may be added to each component as long as the preservative exerts the preservation performance and the preservative does not influence adversely on the performance of the dispersant.

The specific amount of the preservative added can be, for example, not more than 20% by weight, or more preferably not more than 10% by weight. Among the preservatives, polyhydric alcohols such as propylene glycol, butylene glycol, dipropylene glycol, pentylene glycol, and hexylene glycol are particularly preferably used. Two or more compounds selected from the group may be used together. Among them, pentylene glycol or 1,3-butylene glycol is particularly preferably used. In view of the applicability as described above, the amount of any component other than the powder, water, the dispersant, and the preservative is preferably not more than 1%. The glycols are often used as a humectant for cosmetics, and also have antibacterial activity, and therefore have a preservative effect.

The dispersion of the present invention preferably does not contain any components other than the inorganic powder, the dispersant, water, and the preservative. This is because any other component may influence adversely on the stability of the dispersant by being blended in the dispersion. Also, if the dispersion is mixed in a cosmetic, it is undesirable that the dispersion may contain any undesirable compound.

When commercially available products are used as the inorganic powder, the dispersant, water, and the preservative, the products may contain a certain amount of a contaminated component such as an antioxidant or a residual raw material of the products. As described herein, the phrase "does not contain any components other than the inorganic powder, the dispersant, water, and the preservative" encompasses a case where the contaminated component derived from the raw material is contained in an amount of not more than 0.1% by weight. For example, an antioxidant (tocopherol) may be added in some commercially available dispersants. When the antioxidant derived from the raw material is contained in an amount of 0.1% by weight based on the total amount of the composition, the dispersion is corresponds to the composition which "does not contain any components other than the inorganic powder, the dispersant, water, and the preservative".

A method for obtaining the dispersion of the present invention may be any known method as long as the powder can be dispersed uniformly. For example, a method using a bead mill or a high-pressure homogenizer is suitable.

Also, a thin film can be produced by applying the aqueous dispersion obtained by the present invention. For example, a zinc oxide film fixed by silica can be produced by coating a zinc oxide dispersion treated with a silicone, and heat-treating the coating of the dispersion with high heat or plasma. In dispersants for similar zinc oxide dispersions, when a dispersant such as a polyether or a polyether alkyl ether is used, a silicone-covered zinc oxide coating can be produced conveniently by heating the dispersion at a temperature lower than the decomposition temperature of the silicone covering zinc oxide.

Further, the dispersion of the present invention can be mixed in cosmetics, coatings, or inks as such. In this case, cosmetic compositions, water-based coatings, or ink compositions can be obtained by mixing the dispersion with various components used in cosmetics, coatings, or inks. The cosmetics, water-based coatings, or ink compositions are also included in the present invention.

The cosmetics thus obtained can suitably disperse the water-repellent inorganic powder in a water-based composition. Thereby, a water-based composition having stable ultraviolet preventing performance can be obtained. Also, an emulsion in which a powder subjected to a hydrophobization treatment is dispersed in water can be obtained. The cosmetic having such a special configuration is preferred because it provides a texture different from that of the conventional cosmetic in which a powder is dispersed in an oil phase.

The cosmetic is not particularly limited. Cosmetics for ultraviolet prevention such as a sunscreen agent; cosmetics for base make up such as a foundation; and cosmetics for point make up such as a lipstick can be obtained by mixing the dispersion of the present invention with any cosmetic raw material, as necessary.

The cosmetic can be in any form, for example, a form of an oil-based cosmetic, a water-based cosmetic, an O/W type cosmetic, or a W/O type cosmetic. Among them, the dispersion can be suitably used in sunscreen agents.

The cosmetic may contain any water-based component or an oil-based component which can be used in the cosmetic field. The water-based component and the oil-based component may contain any component, including, but not limited to, for example, an oil solution, a surfactant, a humectant, a higher alcohol, a sequestering agent, a natural or synthetic polymer, a water-soluble or oil-soluble polymer, an ultraviolet blocking agent, various extracts, a coloring agent such as an organic dye, a preservative, an antioxidant, a colorant, a thickener, a pH adjuster, a perfume, a cooling-sensation agent, an antiperspirant, a bactericidal agent, a skin activating agent, and various powders.

Examples of the oil solution include, but not limited to, for example, natural animal and plant fats (for example, olive oil, mink oil, castor oil, palm oil, beef tallow, evening primrose oil, coconut oil, castor oil, cacao oil, and macadamia nut oil); waxes (for example, jojoba oil, beeswax, lanolin, carnauba wax, and candelilla wax); higher alcohols (for example, lauryl alcohol, stearyl alcohol, cetyl alcohol, and oleyl alcohol); higher fatty acids (for example, lauric acid, palmitic acid, stearic acid, oleic acid, behenic acid, and lanolin fatty acid); higher aliphatic hydrocarbons (for example, liquid paraffin, solid paraffin, squalane, vaseline, ceresin, and microcrystalline wax); synthetic ester oils (for example, butyl stearate, hexyl laurate, diisopropyl adipate, diisopropyl sebacate, octyldodecyl myristate, isopropyl myristate, isopropyl palmitate, isopropyl myristate, cetyl isooctanoate, and neopentyl glycol dicaprate); and silicone derivatives (for example, silicone oils such as methyl silicone and methyl phenyl silicone). Further, an oil-soluble vitamin, a preservative, or a whitening agent may be blended.

Examples of the surfactant include a lipophilic nonionic surfactant and a hydrophilic nonionic surfactant. Examples of the lipophilic nonionic surfactant include, but not limited to, for example, sorbitan monooleate, sorbitan monoisostearate, sorbitan monolaurate, sorbitan monopalmitate, sorbitan monostearate, sorbitan sesquioleate, sorbitan trioleate, sorbitan fatty acid esters such as diglycerol sorbitan penta-2-ethylhexylate and diglycerol sorbitan tetra-2-ethylhexylate, glycerin fatty acids such as glycerol mono-cottonseed oil fatty acid, glycerol monoerucate, glycerol sesquioleate, glycerol monostearate, α,α'-glycerol oleate pyroglutamate, and glycerol monostearate malate; propylene glycol fatty acid esters such as propylene glycol monostearate; hydrogenated castor oil derivatives; and glycerol alkyl ethers.

Examples of the hydrophilic nonionic surfactant include, but not limited to, for example, POE sorbitan fatty acid esters such as POE sorbitan monooleate, POE sorbitan monostearate, and POE sorbitan tetraoleate; POE sorbit fatty acid esters such as POE sorbit monolaurate, POE sorbit monooleate, POE sorbit pentaoleate, and POE sorbit monostearate; POE glycerin fatty acid esters such as POE glycerin monostearate, POE glycerin monoisostearate, and POE glycerin triisostearate; POE fatty acid esters such as POE monooleate, POE distearate, POE monodioleate, and distearic acid ethylene glycol; POE alkyl ethers such as POE lauryl ether, POE oleyl ether, POE stearyl ether, POE behenyl ether, POE 2-octyl dodecyl ether, and POE cholestanol ether; POE alkyl phenyl ethers such as POE octyl phenyl ether, POE nonyl phenyl ether, and POE dinonyl phenyl ether; Pluaronic types such as Pluronic; POE/POP alkyl ethers such as POE/POP cetyl ether, POE/POP2-decyl tetradecyl ether, POE/POP monobutyl ether, POE/POP hydrogenated lanolin, and POE/POP glycerin ether; tetra POE/tetra POP ethylenediamine condensation products such as Tetronic; POE castor oil hydrogenated castor oil derivatives such as POE castor oil, POE hydrogenated castor oil, POE hydrogenated castor oil monoisostearate, POE hydrogenated castor oil triisostearate, POE hydrogenated castor oil monopyroglutamic acid monoisostearic acid diester, and POE hydrogenated castor oil maleic acid; POE beeswax/lanolin derivatives such as POE sorbit beeswax; alkanolamides such as coconut oil fatty acid diethanolamide, lauric acid monoethanolamide, and fatty acid isopropanolamide; POE propylene glycol fatty acid esters, POE alkylamines, POE fatty acid amides, sucrose fatty acid esters, POE nonyl phenyl formaldehyde condensation products, alkyl ethoxydimethylamine oxides, and trioleyl phosphates.

Any other surfactant may be blended, including, for example, anionic surfactants such as fatty acid soaps, higher alkyl sulfate ester salts, POE lauryl sulfate triethanolamine, and alkyl ether sulfate ester salts; cationic surfactants such as alkyl trimethyl ammonium salts, alkyl pyridinium salts, alkyl quaternized ammonium salts, alkyl dimethyl benzylammonium salts, POE alkylamines, alkylamine salts, and polyamine fatty acid derivatives; and amphoteric surfactants such as an imidazoline-based amphoteric surfactant and a betaine-based surfactant, as long as the surfactant does not affect the stability and skin irritation.

Examples of the humectant include, but not limited to, for example, xylitol, sorbitol, maltitol, chondroitin sulfate, hyaluronic acid, mucoitinsulfuric acid, caronic acid, atelocollagen, cholesteryl-12-hydroxystearate, sodium lactate, bile salt, dl-pyrrolidone carboxylate salts, short chain soluble collagen, (EO)PO adducts of diglycerin, Rosa Roxburghii Fruit extract, yarrow extract, and melilot extract.

Examples of the higher alcohol include, but not limited to, for example, linear alcohols such as lauryl alcohol, cetyl alcohol, stearyl alcohol, behenyl alcohol, myristyl alcohol, oleyl alcohol, and cetostearyl alcohol; and branched alcohols such as monostearyl glycerin ether (batyl alcohol), 2-decyl tetradecinol, lanolin alcohol, cholesterol, phytosterol, hexyldodecanol, isostearyl alcohol, and octyl dodecanol.

Examples of the sequestering agent include, but not limited to, for example, 1-hydroxyethane-1,1-diphosphonic acid, 1-hydroxyethane-1,1-diphosphonic acid tetrasodium salt, sodium citrate, sodium polyphosphate, sodium metaphosphate, gluconic acid, phosphoric acid, citric acid, ascorbic acid, succinic acid, and edetic acid.

Examples of the natural water-soluble polymer include, but not limited to, for example, plant polymers such as gum arabic, tragacanth gum, galactan, guar gum, carob gum, karaya gum, carrageenan, pectin, agar, quince seed (Cydonia oblonga), algae colloid (brown alga extract), starch (rice, corn, potato, wheat), and glycyrrhizinic acid; microbial polymers such as xanthan gum, dextran, succinoglycan, and pullulan; and animal polymers such as collagen, casein, albumin, and gelatin.

Examples of the semisynthetic water-soluble polymer include, but not limited to, for example, starch polymers such as carboxymethyl starch and methyl hydroxypropyl starch; cellulose polymers such as methylcellulose, nitrocellulose, ethylcellulose, methyl hydroxypropyl cellulose, hydroxyethyl cellulose, cellulose sodium sulfate, hydroxypropyl cellulose, sodium carboxymethyl cellulose (CMC), crystalline cellulose, and cellulose powder; and alginate polymers such as sodium alginate and alginic acid propylene glycol ester.

Examples of the synthetic water-soluble polymer include, but not limited to, for example, vinyl polymers such as polyvinyl alcohol, polyvinyl methyl ether, and polyvinylpyrrolidone; polyoxyethylene polymers such as polyethylene glycol 20,000, 40,000, and 60,000; copolymers such as a polyoxyethylene polyoxypropylene copolymer; acrylic polymers such as sodium polyacrylate, polyethyl acrylate, and polyacrylamide; polyethylenimine, cationic polymer, carboxyvinyl polymer, and alkyl-modified carboxyvinyl polymer.

Examples of the inorganic water-soluble polymer include, but not limited to, for example, bentonite, magnesium aluminum silicate (Veegum), laponite, hectorite, and silicic anhydride.

Examples of the ultraviolet blocking agent include, but not limited to, for example, benzoic acid-based ultraviolet blocking agents such as p-aminobenzoic acid (hereinafter abbreviated as PABA), PABA monoglycerin ester, N,N-dipropoxy PABA ethyl ester, N,N-diethoxy PABA ethyl ester, N,N-dimethyl PABA ethyl ester, and N,N-dimethyl PABA butyl ester; anthranilic acid-based ultraviolet blocking agents such as homomenthyl-N-acetyl anthranilate; salicylic acid-based ultraviolet blocking agents such as amyl salicylate, menthyl salicylate, homomenthyl salicylate, octyl salicylate, phenyl salicylate, benzyl salicylate, and p-isopropanol phenyl salicylate; cinnamic acid-based ultraviolet blocking agents such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, and glyceryl mono-2-ethylhexanoyl-diparamethoxy cinnamate; benzophenone-based ultraviolet blocking agents such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methyl benzophenone, 2-hydroxy-4-methoxybenzophenone-5-sulfonate, 4-phenyl benzophenone, 2-ethylhexyl-4'-phenyl-benzophenone-2-carboxylate, 2-hydroxy-4-n-octoxybenzophenone, and 4-hydroxy-3-carboxybenzophenone; 3-(4'-methylbenzylidene)-d,l-camphor, 3-benzylidene-d,l-camphor, urocanic acid, urocanic acid ethyl ester, 2-phenyl-5-methyl benzoxazole, 2,2'-hydroxy-5-methyl phenyl benzotriazole, 2-(2'-hydroxy-5'-t-octylphenyl)benzotriazole, 2-(2'-hydroxy-5'-methylphenyl benzotriazole, dibenzalazine, dianisoylmethane, 4-methoxy-4'-t-butyldibenzoylmethane, and 5-(3,3-dimethyl-2-norbornylidene)-3-pentan-2-one.

Examples of the other chemical component include, but not limited to, for example, vitamins such as vitamin A oil, retinol, retinol palmitate, inosit, pyridoxine hydrochloride, benzyl nicotinate, nicotinamide, DL-α-tocopherol nicotinate, magnesium ascorbyl phosphate, 2-O-α-D-glucopyranosyl-L-ascorbic acid, vitamin D2 (ergocalciferol), dl-α-tocopherol, DL-α-tocopherol acetate, pantothenic acid, and biotin; hormones such as estradiol and ethinyl estradiol; amino acids such as arginine, aspartic acid, cystine, cysteine, methionine, serine, leucine, and tryptophan; anti-inflammatory agents such as allantoin and azulene; whitening agents such as arbutin; astringents such as tannic acid; refrigerants such as L-menthol and camphor; sulfur, lysozyme chloride, and pyridoxine chloride.

Examples of various extracts include, but not limited to, for example, Houttuynia cordata extract, Phellodendron bark extract, melilot extract, dead nettle extract, licorice extract, peony root extract, soapwort extract, luffa extract, cinchona extract, strawberry geranium extract, sophora root extract, nuphar extract, fennel extract, primrose extract, rose extract, rehmannia root extract, lemon extract, lithospermum root extract, aloe extract, calamus root extract, eucalyptus extract, field horsetail extract, sage extract, thyme extract, tea extract, seaweed extract, cucumber extract, clove extract, bramble extract, lemon balm extract, carrot extract, horse chestnut extract, peach extract, peach leaf extract, mulberry extract, knapweed extract, hamamelis extract, placenta extract, thymic extract, silk extract, and licorice extract.

Examples of various powders include luster color pigments such as red iron oxide, yellow iron oxide, black iron oxide, mica titanium, iron oxide-coated mica titanium, and titanium oxide-coated glass flake; inorganic powders such as mica, talc, kaolin, and sericite; and organic powders such as polyethylene powder, nylon powder, crosslinked polystyrene, cellulose powder, and silicone powder. Preferably, some or all of powder components are hydrophobized with a material such as a silicone, a fluorine compound, a metallic soap, an oil solution, or an acyl glutamic acid salt by a known method in order to improve sensory characteristics and makeup retainability. Further, a composite powder other than the inorganic powder subjected to a water-repellent organic surface treatment may be blended and used.

When the dispersion of the present invention is used as a component added to sunscreen inks, examples of the pigment include colored pigments such as titanium oxide, red iron oxide, antimony red, cadmium yellow, cobalt blue, prussian blue, ultramarine, carbon black, and graphite; and extender pigments such as calcium carbonate, kaolin, clay, barium sulfate, aluminium hydroxide, and talc. Further, the dispersion of the present invention can be used with the organic pigment including pigment components such as a soluble azo pigment, an insoluble azo pigment, an azo lake pigment, a condensed azo pigment, a copper phthalocyanine pigment, and a condensed polycyclic pigment; binder resins such as a shellac resin, an acrylic resin, a styrene-acrylic resin, a styrene-maleic acid resin, a styrene-acrylic-maleic acid resin, a polyurethane resin, a polyester resin, and a polyamide resin; and water-miscible organic solvents.

When the dispersion of the present invention is blended in a coating, a resin in the coating may be a curable or uncurable resin. The coating may be a solvent-based coating containing an organic solvent, or a water-based coating in which a resin is dissolved or dispersed in water.

When the dispersion of the present invention is used as a component added to a coating composition, the dispersion can be used with film-forming resins such as an acrylic resin, a polyester resin, and an epoxy resin; various pigments such as a colored pigment, a extender pigment, and a luster pigment; a curing catalyst, a surface control agent, an antifoaming agent, a pigment dispersant, a plasticizer, a film-forming aid, an ultraviolet absorbing agent, an antioxidant, and the like.

Further, water-based coatings and water-based ink compositions thus obtained are preferred in view of stable dispersibility of the water-repellent inorganic powder in a water-based medium.

EXAMPLES

While the present invention will now be described in more detail with reference to the examples, the present invention is not limited to these examples. Unless otherwise noted, in the examples and comparative examples, "%" means % by weight.

To a mayonnaise bottle were charged 86 g of water and 4 g of a dispersant in Table 1, and further 10 g of silicone surface-treated zinc oxide microparticles (manufactured by Sakai Chemical Industry Co., Ltd., FINEX-50S-LP2: particle diameter 20 nm) and 100 g of φ1.5 glass beads were charged. The contents were dispersed with a paint shaker. After separating the beads, aqueous dispersions were each obtained as shown in Table 1.

TABLE 1

| Number | Dispersant | | HLB | Evaluation result Condition of dispersion |
|---|---|---|---|---|
| Example 1 | Polyoxyethylene sorbitan monooleate | Rheodol TW-O120 | 15.0 | ○ |
| Example 2 | Polyoxyethylene sorbit tetraoleate | Rheodol 430 | 10.5 | ○ |
| Example 3 | Polyether derivative | Emulgen A-60 | 12.8 | ○ |
| Example 4 | Polyether-modified silicone | KF-6011 | 14.5 | ○ |
| Example 5 | Polyether-modified silicone | KF-6043 | 14.5 | ○ |
| Comparative Example 1 | Sorbitan monooleate | Rheodol AO-10 | 4.3 | X |
| Comparative Example 2 | Sorbitan sesquioleate | Rheodol AO-15 | 3.7 | X |
| Comparative Example 3 | Polyether-modified silicone | KF-6004 | 9.0 | X |
| Comparative Example 4 | Polyether-modified silicone | KF-6017 | 4.5 | X |
| Comparative Example 5 | Polyoxyethylene alkyl ether | Emulgen 1135S-70 | 17.9 | X |
| Comparative Example 6 | Polyoxyethylene myristyl ether | Emulgen 4085 | 18.9 | X |
| Comparative Example 7 | Polyethylene glycol distearate | Emanon 3199V | 19.4 | X |

○ . . . dispersed uniformly
X . . . separated between water and most of the powder, or foaming or clumping occurs even though the powder is blended in water.
In this table, KF-6011, KF-6043, KF-6004, and KF-6017 are manufactured by Shin-Etsu Chemical Co., Ltd., and the other dispersants are manufactured by Kao Corporation.

Comparative Example 8

To a mayonnaise bottle were charged 86 g of water and 4 g of a polyether-modified silicone (KF-6011: manufactured by Shin-Etsu Chemical Co., Ltd.). To the bottle were charged 10 g of zinc oxide microparticles without silicone surface treatment (manufactured by Sakai Chemical Industry Co., Ltd., FINEX-50: particle diameter 20 nm) and 100 g of φ1.5 glass beads. The contents were dispersed with a paint shaker, and separated from the beads. The mixture foamed heavily, and a uniform aqueous dispersion could not be obtained.

Example 6

To a mayonnaise bottle were charged 86 g of water and 4 g of a polyether-modified silicone (KF-6011: manufactured by Shin-Etsu Chemical Co., Ltd.). To the bottle were charged 10 g of silicone surface-treated, silica/aluminium hydroxide surface-treated titanium oxide microparticles (manufactured by Sakai Chemical Industry Co., Ltd., STR-100A-LP: spindle-shaped particles having a short axis of 20 nm and a long axis of 100 nm) and 100 g of φ1.5 glass beads. The contents were dispersed with a paint shaker to obtain a uniform aqueous dispersion.

A slide glass was each immersed in aqueous dispersions obtained in Examples 1-6 and Comparative Example 8. After the slide glass was picked up, one surface of the slide glass was wiped, and a uniform film was made from the residual liquid at the other surface of the slide glass using a bar coater. After that, the slide glass was dried at 120° C. overnight with a dryer to obtain a dried thin film on the side glass. The transmittances in each wavelength of visible light and UV rays were measured with a spectrophotometer (V-570: manufactured by JASCO Corporation), and the results are shown in FIGS. 1 and 2, and 3 and 4, respectively. An integrating sphere was used in the measurement in the UV region.

The results shown in Table 1 clearly show that the dispersion of the present invention is well dispersed, and can be suitably used for various applications. FIGS. 1, 2, 3, and 4 show that the dispersion of the present invention has high transparency and good ultraviolet cut-off efficiency because of uniform dispersion.

Example 7

To a mayonnaise bottle were charged 64 g of water, 10 g of a polyether-modified silicone (KF-6011: manufactured by Shin-Etsu Chemical Co., Ltd.), and 6 g of 1,3-butylene glycol. To the bottle were charged 20 g of silicone surface-treated, aluminium hydroxide surface-treated titanium oxide microparticles (manufactured by Sakai Chemical Industry Co., Ltd., STR-100C-LP: spindle-shaped particles having a short axis of 20 nm and a long axis of 100 nm) and 100 g of φ1.5 glass beads. The contents were dispersed with a paint shaker to obtain a uniform aqueous dispersion.

Example 8

To a mayonnaise bottle were charged 64 g of water, 10 g of a polyether-modified silicone (KF-6011: manufactured by Shin-Etsu Chemical Co., Ltd.), and 6 g of 1,3-butylene glycol. To the bottle were charged 20 g of silicone surface-treated, silica surface-treated titanium oxide microparticles (manufactured by Sakai Chemical Industry Co., Ltd., STR-100W-LP: spindle-shaped particles having a short axis of 20 nm and a long axis of 100 nm) and 100 g of φ1.5 glass beads. The contents were dispersed with a paint shaker to obtain a uniform aqueous dispersion.

Figure 1:
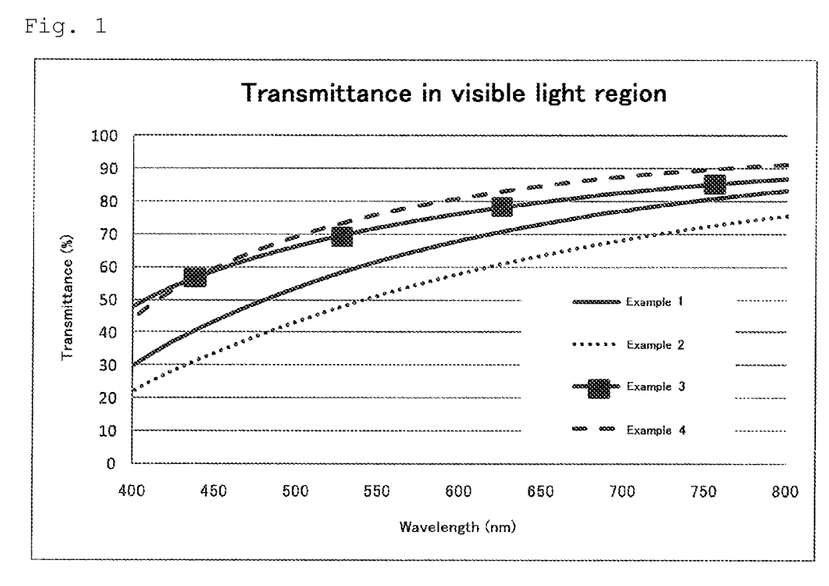
FIG. 1 is a graph showing the transmittance in a visible light region of dispersions according to Examples 1-4.
Figure 2:
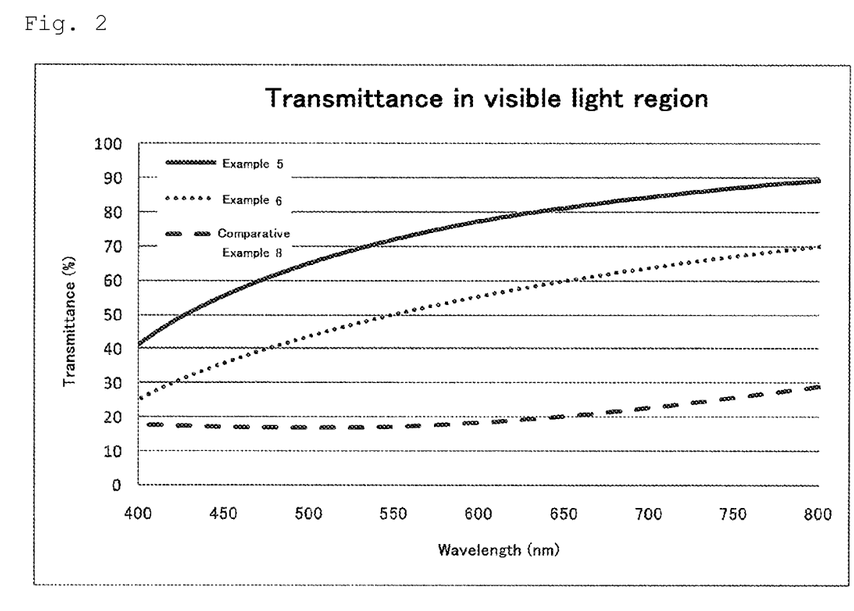
FIG. 2 is a graph showing the transmittance in a visible light region of dispersions according to Examples 5 and 6, and Comparative Example 8.
Figure 3:
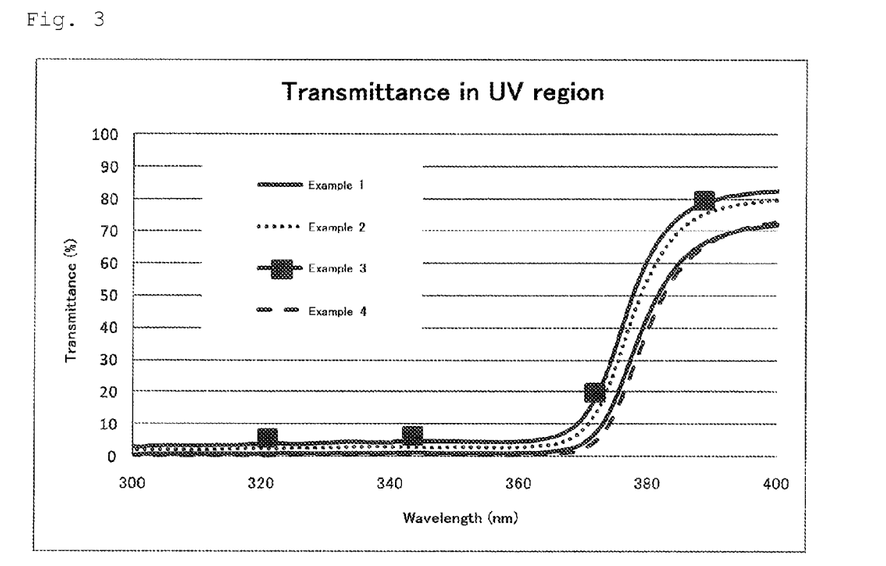
FIG. 3 is a graph showing the transmittance in a UV region of dispersions according to Examples 1-4.
Figure 4:
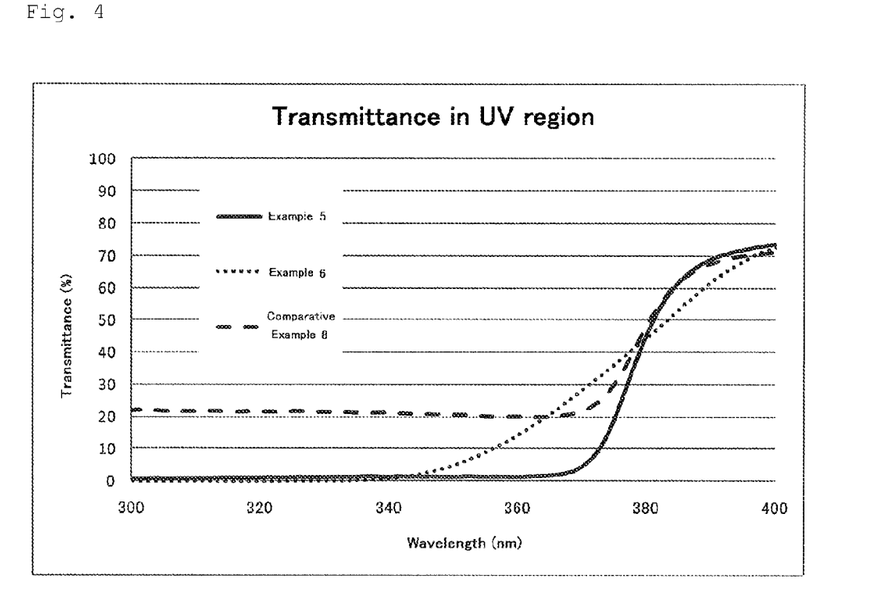
FIG. 4 is a graph showing the transmittance in a UV region of dispersions according to Examples 5 and 6, and Comparative Example 8.
Figure 5:
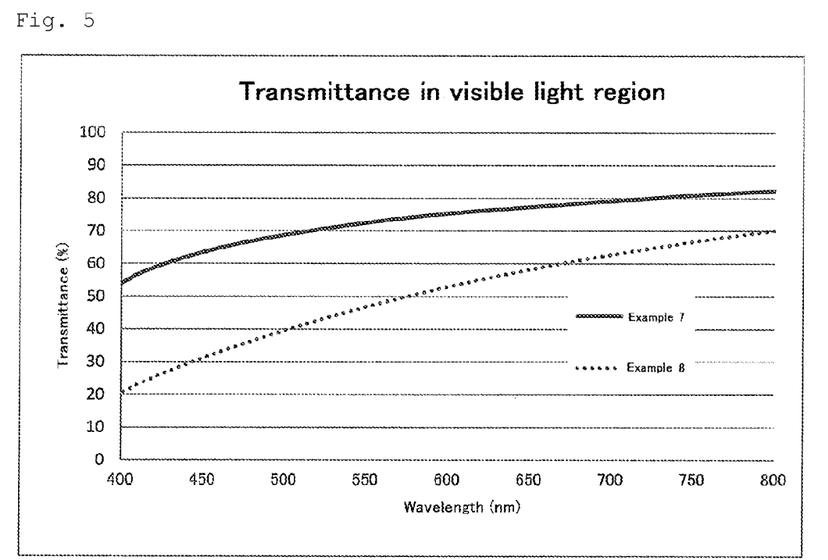
FIG. 5 is a graph showing the transmittance in a visible light region of dispersions according to Examples 7 and 8.
Figure 6:
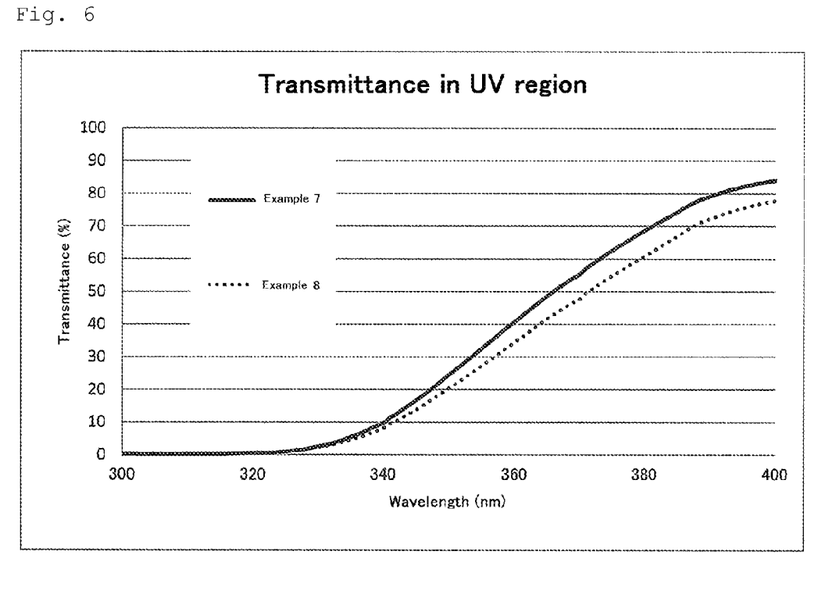
FIG. 6 is a graph showing the transmittance in a UV region of dispersions according to Examples 7 and 8.

A coating film was made on a slide glass by using dispersions obtained in Examples 7 and 8 with a bar coater #2. The optical properties are shown in FIG. 5 (visible light transparency) and FIG. 6 (ultraviolet blocking property: an integrating sphere was used).

Example 9

First, 30 g of isopropyl alcohol and 4 g of isostearic acid PEG-20 (EMALEX PEIS-20EX: manufactured by Nihon-Emulsion Co., Ltd.: HLB value 14) were mixed and dissolved. To the mixture were charged 40 g of silicone surface-treated, silica surface-treated titanium oxide microparticles (manufactured by Sakai Chemical Industry Co., Ltd., STR-100W-LP: spindle-shaped particles having a short axis of 20 nm and a long axis of 100 nm). The mixture was heated with stirring to distil isopropyl alcohol away, thereby obtaining 44 g of a powder treated with the dispersant. In a mixture of 10 g of 1,3-butylene glycol and 46 g of water, 44 g of the powder treated with the dispersant was charged, and dispersed with a homomixer to obtain a uniform aqueous dispersion.

Example 10

First, 5 g of a polyether-modified silicone (KF-6043: manufactured by Shin-Etsu Chemical Co., Ltd.) and 20 g of 1,3-butylene glycol were mixed. To the mixture were charged 50 g of silicone surface-treated, silica surface-treated titanium oxide microparticles (manufactured by Sakai Chemical Industry Co., Ltd., STR-100W-LP: spindle-shaped particles having a short axis of 20 nm and a long axis of 100 nm). The particles were dispersed uniformly with a roller to obtain a roller product. To the roller product was added 25 g of water to obtain a uniform aqueous dispersion.

Example 11

Oil-in-Water Type Suncut Cream

| (components) | weight (%) |
|---|---|
| 1. ethylhexyl methoxy cinnamate | 7.5 |
| 2. diethylamino hydroxybenzoyl hexyl benzoate | 2.0 |
| 3. isotridecyl isononanoate | 13.2 |
| 4. decamethyl cyclopentasiloxane | 3.0 |
| 5. behenyl alcohol | 0.7 |
| 6. polyglyceryl-10 distearate | 1.6 |
| 7. pentylene glycol | 5.0 |
| 8. carbomer (1%) | 10.0 |
| 9. alkyl acrylate copolymer (1%) | 10.0 |
| 10. triethanolamine | 0.2 |
| 11. ethanol | 5.0 |
| 12. purified water | 26.8 |
| 13. dispersion of Example 8 | 15.0 |

(Production Method)

A: The components 1-7 are mixed and dissolved with heating.

B: The components 8-12 are mixed and heated.

C: A is added to B and the resultant is emulsified.

D: The component 13 is added to C to obtain an oil-in-water type suncut cream.

The resulting oil-in-water type suncut cream was found to spread smoothly, give fresh and light feeling without sticky or greasy feeling, have good makeup retainability, and have good stability without any temporal change.

Example 12

Oil-in-Water Type Suncut Cream

| (components) | weight (%) |
|---|---|
| 1. polyacrylic acid-based emulsifier (note 1) | 1.5 |
| 2. 1,3-butylene glycol | 3.0 |
| 3. preservative | 0.1 |
| 4. purified water | 62.4 |
| 5. ethylhexyl methoxy cinnamate | 7.5 |
| 6. dextrin palmitate | 0.5 |
| 7. zinc oxide microparticle silicone dispersion (note 2) | 5.0 |
| 8. crosslinked dimethyl polysiloxane | 5.0 |
| 9. dispersion of Example 10 | 15.0 |

(note 1) polyacrylic acid-based emulsifier; Simulgel EG (manufactured by SEPIC)
(note 2) zinc oxide microparticle silicone dispersion; DIF-3ST (manufactured by Sakai Chemical Industry Co., Ltd.)

(Production Method)

A: The components 1-4 are mixed and homogenized.

B: The components 5 and 6 are mixed and homogenized with heating.

C: The components 7 and 8 are mixed and homogenized.

D: B and C are added to A and the resultant is emulsified.

E: The component 9 is added to D to obtain an oil-in-water type suncut cream.

The resulting oil-in-water type suncut cream was found to spread smoothly, give fresh and light feeling, have good makeup retainability, and have good stability without any temporal change.

Example 13

Water-in-Oil Type Suncut Milky Lotion

| (components) | weight (%) |
|---|---|
| 1. low viscosity silicone oil | 4.0 |
| 2. isotridecyl isononanoate | 10.0 |
| 3. polyether-modified silicone (note 1) | 1.5 |
| 4. organic modified bentonite | 1.0 |
| 5. titanium oxide microparticle silicone dispersion (note 2) | 25.0 |
| 6. zinc oxide microparticle silicone dispersion (note 3) | 35.0 |
| 7. dispersion of Example 5 | 5.0 |
| 8. 1,3-butylene glycol | 3.0 |
| 9. sodium citrate | 0.2 |
| 10. NaCl | 0.5 |
| 11. preservative | 0.1 |
| 12. perfume | 0.1 |
| 13. purified water | residual quantity |

(note 1) polyether-modified silicone; KF-6028 (manufactured by Shin-Etsu Chemical Co., Ltd.)
(note 2) titanium oxide microparticle silicone dispersion; DIS-10A (manufactured by Sakai Chemical Industry Co., Ltd.)
(note 3) zinc oxide microparticle silicone dispersion; DIF-AW4 (manufactured by Sakai Chemical Industry Co., Ltd.)

(Production Method)
A: The components 1-6 are mixed and homogenized.
B: The components 7-11 and 13 are mixed and homogenized.
C: B is added to A and the resultant is emulsified, and the component 12 is added to obtain a water-in-oil type suncut milky lotion.

The resulting water-in-oil type suncut milky lotion was fine in texture, spread smoothly, gave fresh and light feeling without sticky or greasy feeling, caused no whitening of the applied film, had good makeup retainability, and had good stability without any temporal change.

Example 14

Water-in-Oil Type Suncut Cream

| (components) | weight (%) |
|---|---|
| 1. ethylhexyl methoxy cinnamate | 5.0 |
| 2. diethylamino hydroxybenzoyl hexyl benzoate | 1.0 |
| 3. isotridecyl isononanoate | 6.0 |
| 4. decamethyl cyclopentasiloxane | 7.0 |
| 5. alkyl-polyether-co-modified silicone (note 1) | 1.5 |
| 6. dispersion of Example 9 | 5.0 |
| 7. 1,3-butylene glycol | 5.0 |
| 8. ethanol | 8.0 |
| 9. sodium citrate | 0.2 |
| 10. magnesium sulfate | 0.5 |
| 11. purified water | 60.8 |

(note 1) alkyl-polyether-co-modified silicone; KF-6038 (manufactured by Shin-Etsu Chemical Co., Ltd.)

(Production Method)
A: The components 1-5 are mixed and homogenized.
B: The components 6-11 are mixed, dissolved and homogenized.
C: B is added to A and the resultant is emulsified to obtain a water-in-oil type suncut cream.

The resulting water-in-oil type suncut cream was found to be fine in texture, spread smoothly, give fresh and light feeling without sticky or greasy feeling, have good makeup retainability, and have good stability without any temporal change.

Example 15

Oil-in-Water Type Foundation

| (components) | weight (%) |
|---|---|
| 1. stearic acid | 1.0 |
| 2. behenyl alcohol | 0.3 |
| 3. monoglycerol stearate | 0.3 |
| 4. squalane | 10.0 |
| 5. tri(caprylic acid/capric acid) glyceryl | 8.0 |
| 6. sorbitan sesquioleate | 0.5 |
| 7. POE sorbitan monooleate (20EO) | 1.0 |
| 8. alkyl acrylate copolymer emulsion | 2.2 |
| 9. 1,3-butylene glycol | 3.0 |
| 10. triethanolamine | 1.0 |
| 11. preservative | 0.1 |
| 12. purified water | 32.6 |
| 13. silicone-treated titanium oxide | 8.0 |
| 14. silicone-treated red iron oxide | 0.4 |
| 15. silicone-treated yellow iron oxide | 1.0 |
| 16. silicone-treated black iron oxide | 0.1 |
| 17. POE sorbitan monooleate (20EO) | 0.5 |
| 18. 1,3-butylene glycol | 5.0 |
| 19. purified water | 15.0 |
| 20. dispersion of Example 9 | 10.0 |

(Production Method)
A. The components 1-7 are mixed and dissolved with heating.
B. The components 8-12 are mixed and heated.
C. The components 13-16 are added to the components 17 and 18, dispersed with a roller, and the component 19 is added to form an aqueous dispersion.
D. A is added to B and the resultant is emulsified, and C and the component 20 are added to obtain an oil-in-water type foundation.

The resulting oil-in-water type foundation was excellent in the touch, that is, spread smoothly upon use and had no sticky feeling, and was also excellent in the makeup effect, that is, it caused no whitening of the applied film, and had good stability during storage.

Example 16

Water-in-Oil Type Foundation

| (components) | weight (%) |
|---|---|
| 1. decamethyl cyclopentasiloxane | 16.6 |
| 2. isotridecyl isononanoate | 4.0 |
| 3. ethylhexyl methoxy cinnamate | 4.0 |
| 4. polyether-modified silicone (note 1) | 2.0 |
| 5. crosslinked dimethyl polysiloxane | 1.0 |
| 6. silicone-treated titanium oxide | 8.0 |
| 7. silicone-treated red iron oxide | 0.4 |
| 8. silicone-treated yellow iron oxide | 1.0 |
| 9. silicone-treated black iron oxide | 0.1 |
| 10. POE sorbitan monooleate (20EO) | 0.3 |
| 11. 1,3-butylene glycol | 4.0 |
| 12. dispersion of Example 4 | 5.0 |
| 13. 1,3-butylene glycol | 1.0 |
| 14. glycerin | 3.0 |
| 15. magnesium sulfate | 1.0 |
| 16. ethanol | 5.0 |

-continued

| (components) | weight (%) |
|---|---|
| 17. preservative | 0.1 |
| 18. purified water | residual quantity |

(note 1) polyether-modified silicone; ES-5612 (manufactured by Dow Corning Toray Co., Ltd.)

(Production Method)

A. The components 1-5 are mixed and homogenized.
B. The components 6-9 are added to the components 10 and 11, and dispersed with a roller.
C. B and the components 12-18 are mixed and homogenized.
D. C is added to A and the resultant is emulsified to obtain a water-in-oil type foundation.

The resulting water-in-oil type foundation was excellent in the touch, that is, spread smoothly upon use and had no sticky feeling, and was also excellent in the makeup effect, that is, it caused no whitening of the applied film, had very good makeup retainability, and had good stability during storage.

INDUSTRIAL APPLICABILITY

The dispersion of the present invention can be used in coating agents for forming inorganic films, cosmetics, and printing inks.

The invention claimed is:

1. A dispersion in which an inorganic powder subjected to a water-repellent organic surface treatment is uniformly dispersed in water, wherein the contents of a water-repellent inorganic powder, a nonionic polyether modified silicone dispersant having an HLB value of 10 to 17, and water is 80% by weight or more based on the total amount of the dispersion.

2. The dispersion according to claim 1, wherein the water-repellent inorganic powder is an inorganic oxide surface-treated with a water-repellent material, the inorganic oxide having ultraviolet absorption and scattering properties.

3. The dispersion according to claim 1, wherein the water-repellent inorganic powder is an inorganic oxide surface-treated with a reactive surface treating agent.

4. The dispersion according to claim 1, wherein the reactive surface treating agent is at least one selected from the group consisting of a silicone, a silane-based treating agent, and a titanate-based treating agent.

5. The dispersion according to claim 1, wherein the water-repellent inorganic powder is at least one selected from the group consisting of titanium oxide, zinc oxide, iron oxide, cerium oxide, and composites thereof.

6. The dispersion according to claim 1, wherein the amount of the water-repellent inorganic powder is from 10 to 60% by weight based on the total amount of the dispersion.

7. The dispersion according to claim 1, wherein the amount of the polyether modified silicone dispersant is from 2 to 15% based on the total amount of the dispersion.

8. The dispersion according to claim 1, further comprising a preservative.

9. The dispersion according to claim 8, wherein the preservative is a polyhydric alcohol.

10. The dispersion according to claim 9, wherein the polyhydric alcohol is at least one compound selected from the group consisting of propylene glycol, butylene glycol, dipropylene glycol, pentylene glycol, and hexylene glycol.

11. The dispersion according to claim 8, not containing any components other than the water-repellent inorganic powder, the polyether modified silicone dispersant, water, and the preservative.

12. A cosmetic obtained by mixing the dispersion according to claim 1 with any other component.

13. A water-based coating obtained by mixing the dispersion according to claim 1 with any other component.

14. An water-based ink composition obtained by mixing the dispersion according to claim 1 with any other component.

15. The dispersion according to claim 2, wherein the water-repellent inorganic powder is an inorganic oxide surface-treated with a reactive surface treating agent.

16. The dispersion according to claim 2, wherein the reactive surface treating agent is at least one selected from the group consisting of a silicone, a silane-based treating agent, and a titanate-based treating agent.

17. The dispersion according to claim 3, wherein the reactive surface treating agent is at least one selected from the group consisting of a silicone, a silane-based treating agent, and a titanate-based treating agent.

18. The dispersion according to claim 2, wherein the water-repellent inorganic powder is at least one selected from the group consisting of titanium oxide, zinc oxide, iron oxide, cerium oxide, and composites thereof.

19. The dispersion according to claim 3, wherein the water-repellent inorganic powder is at least one selected from the group consisting of titanium oxide, zinc oxide, iron oxide, cerium oxide, and composites thereof.

* * * * *